United States Patent [19]

Schulte et al.

[11] Patent Number: 4,465,839

[45] Date of Patent: Aug. 14, 1984

[54] PROCESS FOR THE PRODUCTION OF HYDANTOINS

[75] Inventors: Bernhard Schulte, Krefeld; Wolfgang Jakob, Moers; Willi Dünwald, Leverkusen; Karl-Heinrich Meyer, Krefeld, all of Fed. Rep. of Germany

[73] Assignee: Bayer Aktiengesellschaft, Leverkusen, Fed. Rep. of Germany

[21] Appl. No.: 437,968

[22] Filed: Nov. 1, 1982

[30] Foreign Application Priority Data

Nov. 11, 1981 [DE] Fed. Rep. of Germany ....... 3144698
Nov. 11, 1981 [DE] Fed. Rep. of Germany ....... 3144697

[51] Int. Cl.$^3$ ............................................ C07D 233/78
[52] U.S. Cl. ..................... 548/310; 536/23; 544/60; 544/82; 544/139; 544/296; 544/322; 544/336; 544/357; 544/370; 546/210; 546/256; 546/278; 548/101; 548/110; 548/309; 548/311; 548/313
[58] Field of Search ............... 548/310, 311, 313, 110, 548/101, 309; 546/278, 210, 256; 536/23; 544/370, 139, 60, 82, 322, 357, 336, 296

[56] References Cited

U.S. PATENT DOCUMENTS 3,254,036   5/1966   Robinson ........................... 528/422
4,246,393   1/1981   Zecher et al. ....................... 528/75

FOREIGN PATENT DOCUMENTS 2662       7/1979   European Pat. Off. .
33477      8/1981   European Pat. Off. .
3144700    5/1983   Fed. Rep. of Germany .
3144701    5/1983   Fed. Rep. of Germany .

Primary Examiner—Richard A. Schwartz
Attorney, Agent, or Firm—Connolly and Hutz

[57] ABSTRACT

The invention relates to a process for the production of compounds containing at least one hydantoin ring by reacting a carbodiimide with derivatives of succinic acid anhydride corresponding to the following general formula:

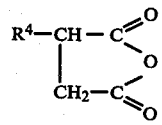

wherein $R^4$ represents a halogen atom, an alkyl-carboxy or aryl-carboxy group; or with maleic acid anhydride in the presence of aromatic OH-functional compounds at temperatures of from about 20° to about 250° C., optionally in a solvent and optionally in the presence of a catalyst, and also to the use of the polyhydantoins obtained, where they have high molecular weights, as high temperature-resistant coating compositions, films, powders, adhesives, lacquers or mouldings.

7 Claims, No Drawings

PROCESS FOR THE PRODUCTION OF HYDANTOINS

This invention relates to a process for the production of compounds containing at least one hydantoin ring in the molecule by reacting carbodiimides with maleic acid anhydride or substituted succinic acid anhydrides and monofunctional or polyfunctional aromatic alcohols.

Hydantoins, polyhydantoins and processes for the production thereof are known (cf, for example, Am. Chem. J. 45, 383; BE-PS No. 678, 282).

Monomolecular hydantoins may be used in the pharmaceutical and plant-protection fields, while polyhydantoins have acquired significance as temperature-resistant coating compositions in the field of electrical insulating lacquers (FR-PS No. 1,484,694).

The present invention relates to a new process for the production of compounds containing hydantoin rings which is characterised in that a carbodiimide is reacted with maleic acid anhydride or with derivatives of succinic acid anhydride corresponding to the following general formula:

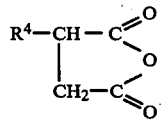

wherein $R^4$ represents a halogen atom, an alkyl-carboxy group or an aryl-carboxy group; in the presence of monofunctional or polyfunctional aromatic OH-functional compounds (such as phenol, cresol or 2,2-bis-(4-hydroxyphenyl)-propane) at temperatures of from 20° to 250° C., optionally in the presence of a catalyst and optionally in the presence of a solvent.

It is known that maleic acid may be converted to maleic acid anhydride by reaction with carbodiimides (J. Prakt. Chem. 79, 513 (1909)) and that organic carbodiimides may be used for removing traces of acid from the corresponding anhydrides (Chem. Abstr. 58, 9254 (1963)), in other words carbodiimides may be regarded as inert to acid anhydrides. It was only at high reaction temperatures, for example in boiling dimethyl formamide, that the formation of N-acyl-N,N'-disubstituted ureas was observed in the reaction of diphenyl carbodiimide with acid anhydrides (Chem. Rev. 67, 2 (1967), page 107; J. Am. Chem. Soc. 21, 136 (1899); Chem. Ber. 89, 2681 (1956)). Hydantoins are not formed in this way.

Surprisingly, hydantoins may be obtained by working in accordance with the present invention and reacting carbodiimides with maleic acid anhydride or with substituted succinic acid anhydrides in the presence of monofunctional or polyfunctional aromatic alcohols.

The production of polyhydantoins may be carried out with particular advantage by the process according to the present invention. In this case, the aromatic alcohol may serve both as a reactant and also as a solvent for the polymeric reaction product. Polymers having very high softening temperatures are obtained, being suitable for use as high temperature-resistant coating compositions, particularly in the field of electrical insulating lacquers.

According to the present invention, monocarbodiimides containing one —N=C=N-group in the molecule, the cyclic dimers or trimers thereof or even linear or branched polycarbodiimides containing more than two carbodiimide groups in the molecule may be used as carbodiimide compounds.

It is preferred to use carbodiimides corresponding to the following general formulae:

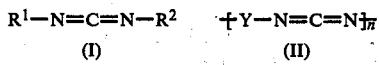

wherein $R^1$ and $R^2$, which may be the same or different, represent an aliphatic radical containing from 1 to 20 carbon atoms, a cycloaliphatic radical containing from 5 to 12 carbon atoms, an aliphatic-aromatic radical containing from 6 to 20 carbon atoms, an aromatic radical containing from 6 to 16 carbon atoms, an aromatic or cycloaliphatic $C_5$–$C_{12}$ radical containing one or more heteroatoms, such as N, O or S, which in either case may optionally be substituted by halogen (preferably chlorine, bromine, iodine or fluorine), nitrile, $C_2$–$C_{12}$ dialkylamino, $C_7$–$C_{12}$ alkyl-arylamino, $C_2$–$C_{18}$ alkoxy-carbonyl, $C_7$–$C_{18}$ aroxy-carbonyl, $C_2$–$C_{18}$ alkyl-carboxy, $C_7$–$C_{18}$ aryl carboxy, $C_1$–$C_{18}$ alkoxy, $C_6$–$C_{18}$ aroxy, $C_1$–$C_{18}$ alkyl or halo-alkyl or nitro groups, or a $C_2$–$C_{12}$ dialkylamino, $C_2$–$C_{10}$ alkoxycarbonyl, $C_6$–$C_{18}$ glycosyl radical or an —Si($R^3$)$_3$—, —Sn($R^3$)$_3$—, —SO$_2R^3$-group (wherein $R^3$ represents $C_6$–$C_{12}$ aryl or $C_1$–$C_8$ alkyl), or which may be attached to one another as members of corresponding cyclic organic radicals;

Y has the same definition as $R^1$ and $R^2$ and preferably represents aliphatic radicals containing from 2 to 12 carbon atoms, cycloaliphatic radicals containing from 5 to 12 carbon atoms, $C_6$–$C_{16}$ aryl radicals or diphenyl radicals attached through O, S, SO$_2$, CH$_2$, CH$_3$—C—CH$_3$ or CO or —Si($R^3$)$_2$— or —Sn($R^3$)$_2$-groups; and n represents an integer of from 2 to 2000, preferably from 2 to 1000.

According to the present invention, the monocarbodiimides used are N,N'-symmetrically and/or asymmetrically substituted aliphatic, aliphatic-aromatic, cyclic, heterocyclic, aromatic compounds optionally containing one or more heteroatoms and containing an N=C=N-group in the molecule, for example dialkyl carbodiimides, such as dimethyl, diethyl, diisopropyl, dihexyl, dibutyl, dinonyl, didodecyl and distearyl carbodiimide, preferably aromatic, optionally substituted monocarbodiimides, such as diphenyl, ditolyl, dinaphthyl carbodiimide, di-(p-iodophenyl), di-(p-dimethylaminophenyl), dipyridyl carbodiimide, dinitro, alkoxy, aroxy, chloro, dichloro, trichloro, tetrachloro, pentachlorophenyl, benzyl, p-bromophenyl carbodiimide or carbodiimes of dibenzoic acid esters, diphthalic acid esters, diisophthalic acid esters, carbodiimide dibenzonitrile, cycloaliphatic carbodiimides, such as dicyclohexyl carbodiimide, and unsaturated carbodiimides, such as diallyl, dioleyl, dicyclohexenyl carbodiimide.

These carbodiimide compounds may be obtained by known methods, for example from the corresponding thioureas, in the presence of metal oxides, mercury salts, sodium salts, aryl sulphochlorides, or by the oxidation of thioureas or from S-alkyl isothioureas, urea compounds as described, for example, in Chem. Rev. 67, 2 (1967), page 107, or from the corresponding isocyanate compounds with elimination of carbon dioxide in the presence of the known catalysts for the elimination of carbon dioxide (FR-PS No. 1,180,307).

In addition, it is possible to use the N-sulphonyl carbodiimides $RSO_2N=C=NR$, the N-aminocarbodiimides $RN=C=N-NR_2$ or the N,N'-disilyl carbodiimides described, for example, in Chem. Rev. 67, 2 (1967), page 107; Angew. Chem. 77, 430 (1965); J. Org. Chem. 29 2816 (1964); Ann. 652, 21 (1962); Z. Anorg. Allgem. Chem. 330, 101 (1964).

Other starting components suitable for use in accordance with the present invention are aliphatic, cycloaliphatic, araliphatic, aromatic and heterocyclic linear or branched polycarbodiimides containing more than two carbodiimide groups and mixtures thereof or polycarbodiimides which have a statistical composition or a block-like structure comprising different structural elements in a sequence of certain length in the polymer molecule and which may therefore contain the abovementioned aliphatic, cycloaliphatic, araliphatic, aromatic and heterocyclic structural units in a variety of ratios arranged both in statistical distribution and also blockwise in the polymer molecule.

Where the above-mentioned polycarbodiimides containing two or more carbodiimide groups in the molecule are synthesised from polyfunctional isocyanates, it is possible to use the catalysts known from the literature (cf, for example, FR-PS No. 1,180,307), for example phospholines, phospholidine sulphides or even organometallic compounds of metals of Groups Ia to IIIa of the Periodic Table of Elements, such as phenyl lithium and diethyl zinc.

The polycarbodiimide compounds according to the present invention may be produced from polyisocyanates of the type comprehensively described, for example, in Annalen 562, pages 75 to 136; Am. Chem. J. 45, 383, De-Os No. 2,714,655; U.S. Pat. No. 3,397,253; EP-PS No. 0 012 379. It is particularly preferred to use mixtures of polytolylene carbodiimides (2,4- and 2,6-substitution products), poly-p-and -m-phenylene, carbodiimides and also polycarbodiimides based on aniline/formaldehyde condensates having a polyphenylenemethylene structure and poly-4,4'-diphenyl ether, poly-p-phenylene, polynaphthylene carbodiimide, polyisophorone carbodiimide, polyhexamethylene carbodiimide, polycumene carbodiimide, polymesitylene carbodiimide and/or mixtures thereof and also block polycarbodiimides, for example having the following structures:

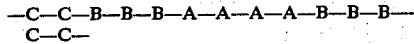

wherein A represents, for example, an aromatic structural element, such as diphenyl methane, B represents an aliphatic radical R, such as the isophorone radical, and C represents an aromatic unit, such as the tolylene or naphthylene group. These block polycarbodiimides may be produced, for example, by successively, subjecting the polyfunctional isocyanates individually used to carbodiimide formation in stages. The indicated structures and commercially readily obtainable bisfunctional isocyanates demonstrate the range of variation in regard to the sequence lengths of and quantitative ratios between the individual elements. The polycarbodiimides may even be branched, for example in cases where trifunctional and higher isocyanates are used in the carbodiimide-forming reactions.

Anhydride compounds suitable for use in accordance with the present invention are substituted succinic acid anhydrides corresponding to the following general formula:

wherein $R^4$ represents halogen, such as chlorine, bromine, iodine, fluorine (preferably chlorine) or the $R^6$—COO-group wherein $R^6$ represents alkyl containing from 1 to 6 carbon atoms or aryl containing from 6 to 10 carbon atoms. It is preferred to use chlorosuccinic acid anhydride and acetoxy succinic acid anhydride which may be obtained, for example, by reacting malic acid with thionyl chloride or acetyl chloride. Maleic acid anhydride is particularly preferred.

Suitable aromatic OH-functional compounds correspond to the following general formula:

$$R^5-(OH)_m \qquad (IV)$$

wherein $R^5$ represents an aromatic radical containing from 6 to 20 carbon atoms which may optionally be substituted one or more times by halogen, preferably chlorine, bromine, iodine or fluorine, $C_1$–$C_8$ alkyl, $C_6$–$C_{12}$ aryl, $C_1$–$C_8$ halo-alkyl, $C_1$–$C_8$ alkoxy, $C_6$–$C_{12}$ aroxy, $C_1$–$C_8$ alkoxy-carbonyl, $C_7$–$C_{15}$ aroxy-carbonyl, $C_2$–$C_8$ alkyl-carboxy, $C_7$–$C_{17}$ aryl-carboxy, $C_1$–$C_6$ alkylamino, $C_2$–$C_{12}$ dialkylamino, amino or nitro groups, or phenyl radicals attached to one another through O, S, $SO_2$, =CH—, —$CH_2$—,

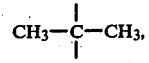

—CO— or —N=N—, cyclohexyl, or the isatin-bis-cresyl or isatin-bis-phenyl radical; and m represents an integer of from 1 to 4, preferably 1 or 2, more preferably 1.

$R^5$ is preferably derived from benzene, toluene, xylene, azobenzene, naphthalene, anthracene, triphenyl methane, diphenyl methane, diphenyl sulphone, diphenoxy, diphenyl sulphide, diphenyl isopropane or diphenyl cyclohexane.

Phenols, cresols xylenols and mixtures thereof are particularly preferred.

The reaction according to the present invention may be illustrated, for example, by the following equations (A) and (B).

A. Using maleic acid anhydride

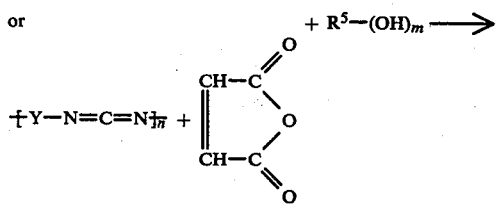
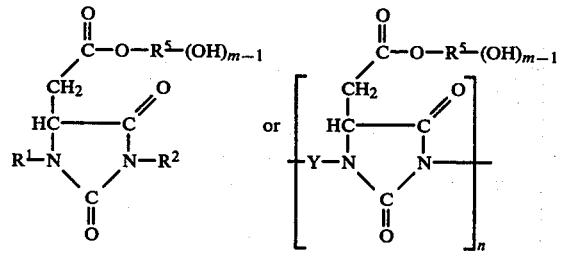

B. Using substituted succinic acid anhydrides:

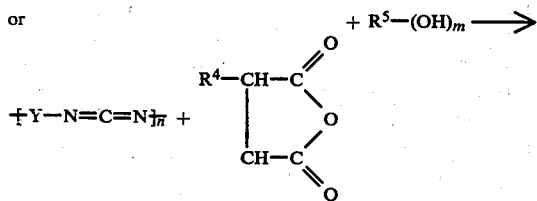
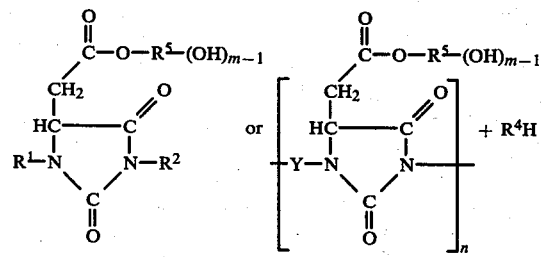

In general, therefore, at least one equivalent of the anhydride, and similarly, at least one equivalent of a monofunctional aromatic alcohol, such as phenol or cresol, are used per equivalent of carbodiimide, the functionality of the hydroxy compound wherein m represents 1 being taken into account where branching, for example of the polymer molecule, is required. However, considerable deviations from these quantitative ratios are also possible.

The hydantoins substituted in the 5-position according to the present invention may be clearly identified by IR-spectroscopy with the aid of the bands typical of hydantoins and aromatic ester carbonyl groups and also by NMR-spectroscopy. The polymeric products generally have solution viscosities of from 200 to 200,000 mPas, preferably from 1000 to 100,000 mPas, as measured on 30%, by weight, solutions in, for example, cresol, butyrolactone, acetophenone, benzoic acid alkyl esters or benzyl alcohol, at a temperature of 25° C.

The reaction according to the present invention may be carried out in solvents which do not react under the reaction conditions or which optionally form loose, further-reacting addition compounds, or as a heterogeneous reaction, i.e. in the presence of diluents, either as such or in suspension or in an excess of one of the reaction components.

The hydroxy compound, such as cresol, phenol or xylenol, is preferably used in excess.

Suitable reaction media are inert organic liquids, for example aliphatic, aromatic hydrocarbons, halogenated hydrocarbons, heterocyclic compounds, esters, lactones, ketones, sulphoxides, sulphones, ethers, substituted amides, nitriles or phosphoric acid amides. Examples thereof are cyclohexane, ligroins, carbon tetrachloride, chloroform, methylene chloride, ethylene chloride, tetrachloroethane, methyl ethyl ketone, diisopropyl ether, ethylene glycol or diethylene glycol dimethyl or diethyl ether, dioxane, tetrahydrofuran, toluene, xylenes, chlorobenzene, dichlorobenzene, acetophenone, cyclohexanone, propylene carbonate, caprolactam, caprolactone, butyrolactone, glycol monomethyl ether acetate, dimethyl sulphoxide, tetramethyl sulphone, benzoic acid alkyl esters, N-methyl pyrrolidone, dimethyl formamide, dimethyl acetamide, hexamethyl phosphoric acid triamide, benzonitrile and mixtures thereof.

Aromatic hydroxy compounds, such as phenols, cresols and xylenols, which according to the present invention may serve both as reactants and also as solvents, are advantageously used.

Combinations of low boiling and relatively high boiling liquids, for example mixtures of methylene chloride/chlorobenzene or o-dichlorobenzene or methylene chloride/xylene or toluene or phenol, are preferably used for the production of monohydantoins.

Ternary mixtures of the above-mentioned solvents or diluents, such as methylene chloride/toluene or xylene/γ-butyrolactone or phenol or cresol, are particularly suitable for the synthesis of the polymeric reaction products. In this connection, the most readily volatile component is suitable for the dissipation of heat by distillation or as an effective solvent for the polycarbodiimides. The relatively high boiling compound, such as toluene, xylene, "Solvesso", may remain partly or completely in the reaction mixture on completion of the reaction by which the polyhydantoin is formed. Accordingly, these components are preferably diluents of the type commonly used in the field of electrical insulating lacquers. The high-boiling component, such as butyrolactone, phenol represents the actual solvent for the reaction product.

Other suitable diluents are cyclohexane and solvent naphtha or, on completion of the reaction of the carbodiimide with the anhydride and the aromatic alcohol, even hydroxy-alkyl ethers or aliphatic, aliphatic-aromatic alcohols, butanol, aminoalcohols, benzyl alcohol, phenoxy ethanol, the methyl, ethyl, isopropyl, butyl monoethers of ethylene, diethylene or propylene glycol, which enable optionally non-polluting, non-phenolic polymer solutions to be produced.

The reaction according to the present invention may be carried out in the presence of catalysts which accelerate the addition of OH-functional compounds onto the carbodiimide group, such as copper-I—chloride, copper-II-chloride, or even in the presence of catalysts suitable for the rearrangement of maleic/fumaric acid, such as iodine, or in the presence of the catalysts known to be suitable for the cyclisation reaction by which the hydantoin ring is formed, such as bases, for example triethylamine, N-methyl morpholine, endoethylene piperazine, acids, for example acetic acid, p-toluene sulphonic acid, metals, particularly iron, lead, zinc, tin, copper, cobalt, titanium, manganese, for example titanium tetrabutylate, titanium aminoalcohol, iron acetylacetonate, dibutyl tin laurate, lead acetate, lead naphthenate, lead ethyl hexoate, tin octoate or calcium naphthenate.

Iodine, endoethylene piperazine (diazabicyclooctane) and catalysts of the type used for forming the carbodiimides, for example phospholine oxide, are particularly suitable.

In some cases, the reaction may even be carried out in the absence of catalysts of the type described above.

In cases where carbodiimides obtained in known manner from isocyanates (cf, for example, DE-AS No. 1,122,057; U.S. Pat. No. 2,941,983) are used, it is possible directly to use the reaction mixture, including the catalyst present therein, if any.

To carry out the process according to the present invention, the carbodiimides, preferably in solution or suspension, are maintained at temperatures of from 20° to 250° C., preferably from 30° to 200° C., for from a few minutes to several hours with maleic acid anhydride or the substituted succinic acid anhydrides in the presence of the aromatic hydroxy compound.

The progress of the reaction may be followed by IR-spectroscopy.

The three reaction components are preferably combined at low temperatures of from 20° to 50° C., optionally with cooling, and one of the reactants is introduced in portions, preferably at from 20° to 45° C. It is possible initially to introduce both the carbodiimides in the form of solutions or suspensions or the anhydride compounds or even the aromatic alcohol, optionally together with the anhydride, with or without more solvent.

In the production of polyhydantoins on a commercial scale, it is advantageous initially to introduce the carbodiimides in the formation of carbodiimides from polyfunctional isocyanates because, after they have been produced, the carbodiimides may be immediately further reacted to form the hydantoin according to the present invention.

In cases where the polycarbodiimides used have a block-structure —B—A—B— (A and B representing sequences of different chain members), a diisocyanate (for example 4,4'-diisocyanato-diphenyl methane) is generally subjected to carbodiimide formation in the above-mentioned reaction media, suitable for the production of monohydantoins, of a readily volatile and substantially involatile liquid, such as methylene chloride/toluene, until an almost complete conversion is obtained. Thereafter, the diisocyanate or even, for example, triisocyanate containing the structural unit B (for example isophorone or tolyl) is added, optionally along with more solvent/diluent, and carbodiimide formation continued, in which case monoisocyanates (for example phenyl, tolyl, naphthyl, cyclohexyl, methyl, cyclohexenyl, oleyl isocyanate, isocyanatobenzoic acid esters, phthalic acid esters, isophthalic acid esters) may then be advantageously introduced as regulators as formation of the polycarbodiimide continues. In the same manner other known blocking reagents can be used (U.S. Pat. No. 2,941,983).

Thereafter, the anhydrides and aromatic hydroxy compounds may be reacted by adding them optionally simultaneously or successively or together in solution in the suitable reaction media mentioned above.

Where phenols, cresols and xylenols are used, it is advantageous initially to add the stoichiometrically necessary quantity or an excess to the carbodiimide introduced beforehand, followed by the addition in portions of the anhydride. More phenol, for example, is added as the reaction progresses if this reaction component is also intended to serve as solvent.

The progress of the reaction to the hydantoin stage is advantageously accomplished by increasing the reaction temperature in stages. It is possible to add inhibitors, such as toluhydroquinone, to prevent polymerisation of the double bond.

The reaction is preferably carried out under an inert gas, such as nitrogen or argon.

The reaction according to the present invention may be carried out either continuously or in batches under normal pressure or under excess pressure.

The low molecular weight reaction products may be worked-up by conventional methods, such as crystallisation or dissolution and reprecipitation.

The monomolecular hydantoins obtainable by the process according to the present invention show activity in the pharmaceutical and plant-protection fields.

The polyhydantoins according to the present invention are distinguished by the particularly high temperature resistance thereof. For example, in the testing of a copper wire coated with these polyhydantoins in accordance with DIN 46 453, softening temperatures above 450° C. are observed. In addition, the polymeric reaction products show excellent solubility and outstanding levelling properties in the coating of electrical conductors and are suitable for use as adhesives, lacquers, films, powders, fibres and mouldings. The properties thereof may be varied within wide limits by the addition of fillers, pigments and low molecular and/or high molecular weight components, for example for the production of lacquers and films. The known polycondensates modified with the polymers according to the present invention, such as polyurethanes, polyamide imides, polyesters, polyester imides, polyamide imides, polyhydantoins, polycarbonates, which are mixed in or precondensed and/or co-condensed optionally using, for example, polycarboxylic acids, anhydrides, esters, polyols, in the production of the polyhydantoins in accordance with the present invention, show considerably improved temperature behaviour and considerably improved levelling properties in cases where products modified in this way are used for coating heat-resistant substrates.

The quantities in which these additives are used may vary considerably according to the particular application envisaged. Quantities of from 5 to 500%, by weight, are preferably used, based on the polyhydantoin according to the present invention.

The polyhydantoins according to the present invention are particularly suitable for stoving lacquers, particularly for wire lacquers and electrical insulating lacquers, the solids content of the possible lacquer solutions processed using conventional lacquering machines and also in the form of impregnating lacquers being variable within wide limits and preferably amouting to from 20 to 80%.

EXAMPLE 1

A. Polydiphenyl methane carbodiimide 0.5 g of a mixture of 1-methyl-1-phospha-2-cyclopentene-1-oxide and 1-methyl-1-phospha-3-cyclopentene-1-oxide is added at room temperature to a solution of 75 g (0.3 mole) of 4,4'-diisocyanatodiphenyl methane and 0.5 g of phenyl isocyanate in 60 g of toluene and 80 g of xylene. With the reaction vessel connected to a gas meter, its contents are heated for approximately 2.5 hours to from 65° to 70° C., resulting in the formation of a highly viscous polycarbodiimide suspension showing the typical IR-bands at 2100/2130 cm$^{-1}$. The quantity of $CO_2$ given off is measured at from 7 to 7.5 liters.

B. Polyhydantoin

Because of stirring problems, the polycarbodiimide suspension (A) is cooled as quickly as possible to about 45° C. and diluted by the addition of 100 g of phenol. first, 29.4 g of maleic acid anhydride (0.3 mole) and then, all at once, 115 g of phenol are introduced at 35° C., after which the sump temperature is increased to from 80° to 85° C. by heating with intensive stirring for about 30 minutes.

The reaction mixture is then heated to from 180° to 185° C. over a period of 3 hours, during which the toluene/xylene mixture distills off. The temperature of from 180° to 185° C. is maintained for 4 hours, a total of approximately 149 g of distillate being removed and 50 g of cresol being added during the increase in viscosity. A clear red-brown polymer solution having a solids content of 34.1% (stoved for 5 minutes at 360° C.) is obtained. It has a viscosity of 3740 mPas (as measured at 20° C. using a Hoppler viscometer after dilution with cresol to a solids content of 15%). The IR-bands typical of hydantoin structures are observed in solution at 1750-1760, 1710 and 1430 (ring band) cm$^{-1}$. The polyhydantoin ester is obtained in the form of a white-brown powder by precipitation from methanol.

The polymer shows the following signals in the NMR-spectrum (CDCl$_3$):

| aromatic protons | $\delta$ = 6.75–7.5 ppm (approx. 13 H) |
|---|---|
| $-\overset{\|}{\underset{\|}{CH}}-$ | $\delta$ = 4.9 ppm (1 H) |
| $-\phi-CH_2-\phi-$ | $\delta$ = 3.95 ppm (2 H) |
| $-CH_2-\overset{O}{\overset{\|\|}{C}}-$ | $\delta$ = 3.2 ppm (2 H) |

The aromatic phenyl ester group in the 5-position of the hydantoin ring is confirmed by elemental analysis:

| (C$_{24}$H$_{18}$N$_2$O$_4$)$_n$ (398)$_n$ | | |
|---|---|---|
| | Calculated | Observed |
| C | 72.3 | 71.7 |
| H | 4.52 | 4.5 |
| N | 7.04 | 7.07 |

The coating of a 0.7 mm diameter copper wire with the polyhydantoin solution prepared in accordance with Example 1 in the form of an approximately 22% solution (diluted with cresol/xylene 1:1) using a wire lacquering machine (application by spray nozzles) takes place with excellent levelling properties of the lacquer. For wire speeds of 8, 10 and 12 meters per minute and stoving temperatures of 400° C, the lacquered wire shows softening temperatures above 470° C., heat shock values of at least 260° C., edge fibre elongations of from 67 to 88% an abrasion resistance equivalent to more than 60 double strokes, a film hardness of at least 5 H, a dielectric strength of at least 8 KV and a high resistance to chemicals.

Testing of the lacquered wire is carried out in accordance with DIN 46 453.

EXAMPLE 2

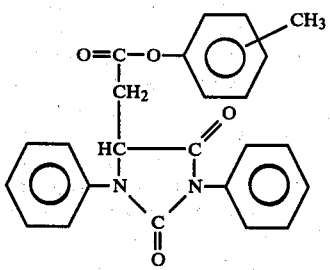

64.7 g of a 30% diphenyl carbodiimide solution in o-dichlorobenzene (IR-bands of the carbodiimide group at 2100/2130 cm$^{-1}$) are initially introduced. 9.8 g (0.1 mole) of maleic acid anhydride are introduced at room temperature, after which 50 g of cresol are added over a period of about 30 minutes with stirring at from 30° to 40° C. The temperature is then increased to 180° C. over a period of 3 hours and maintained thereat for another 3 hours.

Some of the solvent is then removed at a sump temperature of from 120° to 140° C. in a water jet pump vacuum and the reaction product is isolated in the form of a light brown solid by precipitation from a mixture of water and n-propanol, followed by drying. It shows the IR-bands typical of hydantoin rings with lateral aromatic ester groups at 1765/1720/1390–1400 cm$^{-1}$ with the aromatic carbonyl ester band at 1755 cm$^{-1}$. For further purification, the reaction product is dissolved in and reprecipitated from water/n-propanol. Incorporation of the cresol and, hence, the assumed structure are confirmed by NMR-spectroscopy.

| Analysis: C$_{24}$H$_{20}$N$_2$O$_4$ (400) | | |
|---|---|---|
| | C | H | N |
| Calculated: | 72.0 | 5.0 | 7.0 |
| Observed: | 72.6 | 5.3 | 6.9 |

EXAMPLE 3

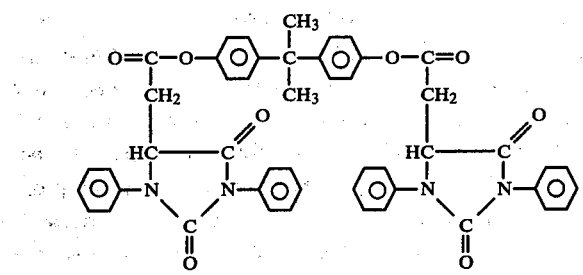

9.8 g (0.1 mole) of maleic acid anhydride and 11.4 g (0.05 mole) of 2,2-bis-(4-hydroxyphenyl)-propane are introduced at room temperature into 40 g of methylene chloride and 80 g of o-dichlorobenzene. 80.8 g of a 24% diphenyl carbodiimide solution in toluene and 100 mg of toluhydroquinone are then added over a period of 30 minutes with stirring at from 40° to 45° C. The temperature is then increased to 120° C. over a period of 2 hours, during which the methylene chloride/toluene mixture distills off, and following the addition of 100 mg of diazabicyclooctane, 50 g of γ-butyrolactone and 100 mg of p-toluene sulphonic acid the reaction mixture is heated for another 2 hours to 180° C. After stirring for 2 hours at 180° C., some of the solvent is distilled off in vacuo and the reaction product isolated by precipitation in isopropanol/H$_2$O. After drying, 21 g of reaction product are obtained in the form of a grey-brown powder, showing the IR-bands characteristic of hydantoins containing lateral aromatic ester groups in the 5-position at 1765, 1720, 1395–1400 cm$^{-1}$ and the aromatic carbonyl ester band at 1755 cm$^{-1}$. After further dissolution in and reprecipitation from isopropanol, the assumed structure is confirmed by the NMR-spectrum.

| Analysis: C$_{49}$H$_{40}$N$_4$O$_8$ (812) | | | |
|---|---|---|---|
| | C | H | N |
| Calculated: | 72.4 | 4.9 | 6.9 |
| Observed: | 72.9 | 4.6 | 6.8 |

EXAMPLE 4

A block polycarbodiimide (structure —B—B—A—A—A—A—B—B) of 50 mole percent of poly-diphenyl methane carbodiimide (A) and 50 mole percent of poly-2,4- (80%) and 2,6- (20%) tolyl carbodiimide (B) containing approximately 0.3 mole of carbodiimide groups (produced by subjecting 37.5 g (0.15 mole) of the diisocyanate of A and then 32.4 g (0.15 mole) of the diisocyanate of B to carbodiimide formation in stages by heating in 150 g of methylene chloride and 100 g of toluene in the presence of 0.75 g of methyl phospholine oxide and in the presence of 2.6 g (0.015 mole) of tolyl isocyanate as regulator) is initially introduced in the above-mentioned solvent/diluent.

100 g of phenol and 50 g of cresol are stirred in at from 40° to 45° C., after which 29.4 g (0.3 mole) of maleic acid anhydride are introduced in portions over a period of about 30 minutes at from 35° to 45° C. The mixture is then heated for 4 hours to 180° C., accompanied by distillation, a solvent mixture of 60 g of phenol and 60 g of cresol being added for dilution as the viscosity increases. The reaction temperature of from 175° to 180° C. is maintained for 4 hours, during which a total of about 270 g of distillate accumulates. A brown-red polymer solution having a solids content of 32.3% (stoved for 5 minutes at 360° C.) and a viscosity of 1640 mPas (as measured at 20° C. after dilution with cresol to a solids content of 15%) is obtained. The IR-bands characteristic of hydantoin rings containing lateral aromatic ester groups are observed in phenolic solvents at 1750–1765, 1710 and 1415–1430 cm$^{-1}$.

The stoving of samples of this polymer solution on metal test plates for 10 minutes at 200° C. and 360° C. gives brown-yellow, clear elastic lacquer films.

After the coating of a copper wire (0.7 mm diameter, vertical wire lacquering machine, oven length 4 meters) with this approximately 24% polyhydantoin solution (diluted with cresol/xylene), lacquered wires which, according to DIN 46 453, have softening temperatures above 400° C., heat shock values of at least 260° C. and dielectric strengths of 7–8 KV are obtained at a stoving temperature of 400° C. and at wire speeds of 8, 10 and 12 meters per minute. The coatings are very smooth by virtue of the excellent levelling properties of the lacquer.

EXAMPLE 5

A block polycarbodiimide (structure (D—D—D—D—C)$_2$) of 20 mole percent of poly-naphthylene carbodiimide (C) and 80 mole percent of poly-diphenyl methane carbodiimide (D) containing approximately 0.4 mole of carbodiimide groups (produced by subjecting 17.1 g (0.08 mole) of the diisocyanate of C and 80 g (0.32 mole) of the diisocyanate of D to carbodiimide formation in stages in 200 g of γ-butyrolactone and 200 g of methylene chloride using 3.4 g (0.02 mole) of naphthyl isocyanate as regulator towards the end of the carbodiimide-forming reaction) is initially introduced.

65 g (0.6 mole) of m-cresol 70 and 39.2 g (0.4 mole) of maleic acid anhydride in 100 g of γ-butyrolactone and 100 g of N-methyl pyrrolidone are introduced with intensive stirring at from 30° to 45° C. The reaction temperature is then increased to 180° C. over a period of 3 hours, during which the methylene chloride distills off. The mixture is then stirred for 4 hours at from 175° to 185° C., 50 g of γ-butyrolactone and 50 g of benzyl alcohol being introduced as the viscosity increases.

A brown-red, non-polluting non-phenolic polymer solution having a solids content of 26.8% (stoved for 5 minutes at 360° C.) and a viscosity of 1120 mPas (as measured at 20° C. after dilution with N-methyl pyrrolidone to a solids content of 15%) is obtained. The polymer precipitated from methanol shows the IR-bands typical of hydantoin rings containing lateral aromatic ester groups at 1770, 1755, 1720 and 1405 cm$^{-1}$.

Application of the polymer solution to a 0.7 mm diameter copper wire at 400° C./10–12 meters per minute using a wire lacquering machine (oven length 4 meters) produces elastic, clear coatings characterised by good levelling properties and having softening temperatures above 400° C. Testing of the lacquered wire is carried out in accordance with DIN 46 453.

EXAMPLE 6

A poly-diphenyl methane carbodiimide solution containing approximately 0.36 mole of carbodiimide groups and showing the typical IR-bands at 2140/2110 cm$^{-1}$ (obtained by subjecting 100 g (0.4 mole) of 4,4'-diisocyantodiphenyl methane to carbodiimide formation by heating to from 45° to 50° C. in 100 g of methylene chloride and 125 g of toluene in the presence of 0.75 g of methyl pholine oxide and 7.5 g (0.08 mole) of phenol as regulator until there is no further evolution of gas) is initially introduced.

150 g of phenol are stirred in at 40° C. and 34.3 g (0.35 mole) of maleic acid anhydride together with 50 g of phenol are introduced in portions over a period of 45 minutes at from 30° to 45° C. The temperature is then increased to 140° C. over a period of 2 hours, during which the toluene/methylene chloride mixture distills off. 7.7 g (0.04 mole) of trimellitic acid anhydride are then introduced at from 120° to 125° C., after which the sump temperature is increased over a period of 2 hours to 180° C. and maintained thereat for 4 hours, during which a total of about 230 g of distillate is removed. 100 g of m-cresol 70 and 20 g of phenol are added as the viscosity increases. After cooling to 130° C., 15 g of xylene are stirred in and a clear, red-brown polymer solution having a solids content of 35.5% (5 minutes at 360° C.) and a viscosity of 1850 mPas (as measured at 20° C. after dilution with m-cresol 70 to a solids content of 15%) is obtained. The high solids content confirms the incorporation of the phenol in the polymer molecule as a lateral aromatic ester group of the hydantoin rings. The polymer isolated by precipitation and dissolution and in reprecipitation from methanol shows the characteristic IR-bands at 1765/1720/1390–1400 cm$^{-1}$ and the aromatic carbonyl ester band at 1755 cm$^{-1}$.

0.7 mm diameter copper wires coated with this lacquer solution in a concentration of approximately 24% (diluted with cresol/xylene 1:1) at 8 and 10 meters per minute in a 4 meters long oven are tested in accordance with DIN 46 453 and have softening temperatures of at least 400° C., a heat shock value of at least 260° C., good elasticity values and a high resistance to chemicals coupled with excellent levelling properties of the lacquer on application.

EXAMPLE 7

61.8 g of polydiphenyl methane carbodiimide (0.3 mole of carbodiimide groups) containing 1.75 g (0.015 mole) of terminal phenyl carbodiimide groups in 100 g of methylene chloride and 100 g of toluene are initially introduced. 200 g of phenol are stirred in at from 35° to 40° C. 47.4 g (0.3 mole) of acetoxy succinic acid anhydride are then added in portions over a period of 30 minutes with intensive stirring. After the addition of 200 mg of toluhydroquinone, the reaction mixture is heated over a period of 5 hours to from 180° to 185° C. accompanied by distillation. It is then stirred for approximately 3 hours at that temperature, approximately 245 g of distillate being obtained and 80 g of m-cresol 70 being added during the increase in viscosity. The acetic acid formed by ester pyrolysis is detected in the distillate. The brown-red clear polymer solution has a solids content of 33.2% (5 minutes at 360° C.), thus confirming incorporation of the phenol in the polymer molecule. The NMR-spectrum of the product precipitated and dissolved in and reprecipitated from methanol shows consistency with the data indicated in Example 1. The lacquer solution obtained has a viscosity of 640 mPas (as measured at 20° C. after dilution with cresol to a solids content of 15%) and the IR-bands typical of aromatic hydantoin esters at 1750–1765, 1710 and 1415–1430 cm$^{-1}$.

The stoving of samples of this polymer solution on test plates at 200°, 300° and 360° C. gives clear, brown-red elastic polymer films.

EXAMPLE 8

A polycarbodiimide suspension of 75 mole percent of polydiphenyl methane carbodiimide and 25 mole percent of poly-2,4- (80%) and 2,6- (20%) carbodiimide with statistical distribution of the structural units and containing approximately 0.4 mole of carbodiimide groups (obtained by subjecting a mixture of 75 g (0.3 mole) of 4,4'-diisocyantodiphenyl methane and 17.4 g (0.1 mole) of a mixture of 2,4- and 2,6-tolylene diisocyanate to carbodiimide formation in 100 g of methylene chloride and 120 g of toluene in the presence of 0.5 g of methylene pholine oxide and 2.38 g (0.02 mole) of phenyl isocyanate as regulator) is initially introduced. 150 g of m-cresol 70 are introduced with intensive stirring at from 30° to 40° C. 53.8 g (0.4 mole) of chlorosuccinic acid anhydride in 100 g of m-cresol are then added over a period of 30 minutes. After the addition of 100 mg of toluhydroquinone, the mixture is heated to 180° C. over a period of 4 hours, during which the methylene chloride and toluene distill off. After stirring for 6 hours, during which 50 mg of phenol are added for dilution as the viscosity increases, a polymer solution having the IR-bands typical of hydantoin rings (1750–1770, 1410–1430 cm$^{-1}$) a viscosity of 480 mPas (stoved for 5 minutes at 360° C.) and a solids content of 36% is obtained.

The thermal elimination of hydrogen chloride is confirmed by connecting up a washing bottle filled with amine solution and the NMR-spectrum of the polymer precipitated and dissolved in and reprecipitated from methanol shows the incorporation of the cresol as a lateral aromatic ester group to the hydantoin ring, which is confirmed by the measured solids content of 36% (5 minutes at 360° C.).

Samples of the lacquer solution stoved at 360° C. produce clear elastic polymer films.

EXAMPLE 9

A solution of 98 g of maleic acid anhydrides in 188 g of phenol is introduced with cooling at 55° C. into a carbodiimide solution of 250 g of 4,4'-diisocyanatodiphenyl methane, 6 g of phenyl isocyanate and 1.5 g of methyl pholine oxide in 250 g of methylene chloride and 250 g of toluene. 300 g of phenol are then added, the temperature increased to 180° C. and 310 g of phenol/cresol (1:1) subsequently introduced. After 3 hours at 180° C., a 33% solution of the polyhydantoin phenyl ester having a viscosity 25 of 54,000 mPas and the IR bands characteristic of hydantoins at 1705 and 1755 cm$^{-1}$ is obtained.

A copper wire lacquered in accordance with Example 1 shows good levelling properties, a maximum edge fibre elongation of 88% and a softening temperature of 475° C.

We claim:

1. A process for the production of hydantoin compounds of the formula

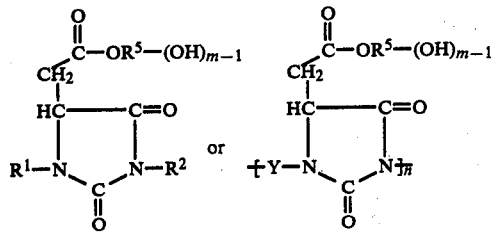

which comprises reacting a carbodiimide of the formula

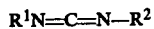
$$R^1N=C=N-R^2$$

or

$$[Y-N=C=N_n]$$

with an acid anhydride of the formula

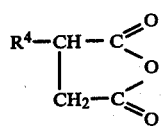

and with a compound of the formula $R^5$—OH at a temperature from about 20° to about 250° C., wherein $R^1$ and $R^2$ are both the same or are different and each is an aliphatic moiety containing from 1 to 20 carbon atoms, a cycloaliphatic moiety containing from 5 to 12 carbon atoms, an aliphatic-aromatic moiety containing from 6 to 20 carbon atoms, an aromatic moiety containing from 6 to 16 carbon atoms, a $C_2$–$C_{12}$ dialkylamino-, $C_2$–$C_{10}$ alkoxy-carbonyl-, $C_6$–$C_{18}$ glycosyl, —Si($R^3$)$_3$—, —Sn($R^3$)$_3$—, —SO$_2R^3$, a heteroaromatic moiety having at least one nitrogen, oxygen or sulfur hetero-atom and from 5 to 12 carbon atoms or a heterocycloaliphatic moiety having at least one nitrogen, oxygen or sulfur hetero-atom and containing from 5 to 12 carbon atoms with the heteroaromatic or hetero-cycloaliphatic being unsubstituted or substituted by at least one substituent selected from halogen, nitrile, $C_2$–$C_{12}$ dialkylamino-, $C_7$–$C_{12}$ alkyl arylamino-, $C_2$–$C_{18}$ alkoxy-carbonyl-, $C_7$–$C_{18}$ aroxy-carbonyl-, $C_2$–$C_{18}$ alkyl-carboxy-, $C_7$–$C_{18}$ aryl-carboxy, $C_1$–$C_{18}$ alkoxy-, $C_6$–$C_{18}$ aroxy-, $C_1$–$C_{18}$ alkyl-, $C_1$–$C_{18}$ halo-alkyland nitro;

$R^3$ is $C_6$–$C_{12}$ aryl or $C_1$–$C_8$ alkyl;
$R^4$ is halogen or $R^6$COO—;
$R^5$ is an aromatic moiety having 6 to 20 carbon atoms unsubstituted or substituted by at least one substituent selected from halogen, $C_1$–$C_8$ alkyl, $C_6$–$C_{12}$ aryl, $C_1$–$C_8$ halo-alkyl, $C_1$–$C_8$ alkoxy, $C_6$–$C_{12}$ aroxy, $C_1$–$C_8$ alkoxy-carbonyl, $C_7$–$C_{15}$ aroxy-carbonyl, $C_2$–$C_8$ alkyl-carboxy, $C_7$–$C_{17}$ aryl-carboxy, $C_1$–$C_6$ alkylamino, $C_2$–$C_{12}$ dialkylamino, amino and nitro; a plurality of phenyl moieties bonded to one another through —O—, —S—, —SO$_2$—, =CH—, —CH$_2$—,

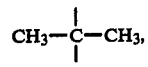

—CO— or —N=N—;
cyclohexyl;
isatin-bis-cresyl; or
isatin-bis-phenyl;
$R^6$ is $C_1$–$C_6$ alkyl or $c_6$–$C_{10}$ aryl;
Y is a divalent moiety having the same definition as $R^1$ and $R^2$;
m is an integer from 1 to 4; and
n is an integer from 2 to 2000.

2. The process according to claim 1 wherein the carbodiimide is polydiphenyl methane carbodiimide, the acid anhydride is maleic anhydride and $R^5$—OH is phenol.

3. The process according to claim 1 wherein the carbodiimide is diphenyl carbodiimide, the acid anhydride is maleic anhydride and $R^5$—OH is cresol.

4. The process according to claim 1 wherein the carbodiimide is diphenyl carbodiimide, the acid anhydride is maleic anhydride and $R^5$—OH is 2,2-bis-(4-hydroxyphenyl)-propane.

5. The process according to claim 1 wherein the carbodiimide is a homopolycarbodiimide, a copolycarbodiimide or a block polycarbodiimide of the formula

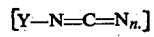
$$[Y-N=C=N_n.]$$

6. The process according to claim 5 wherein the carbodiimide is a block polycarbodiimide comprising blocks of the structure

—BBAAAABB— wherein A is a polydiphenyl methane carbodiimide unit and B is a mixed poly-2,4- and 2,6-tolyl carbodiimide unit.

7. The process according to claim 5 wherein the carbodiimide is a block polycarbodiimide comprising blocks of the structure

wherein C is a poly-naphthylene carbodiimide unit and D is a poly-diphenyl methane carbodiimide unit.